United States Patent [19]

Locko

[11] Patent Number: 4,913,349

[45] Date of Patent: Apr. 3, 1990

[54] DEVICE FOR DISPENSING VOLATILE FRAGRANCES

[75] Inventor: George A. Locko, Savannah, Ga.

[73] Assignee: Union Camp Corporation, Wayne, N.J.

[21] Appl. No.: 280,006

[22] Filed: Dec. 5, 1988

Related U.S. Application Data

[63] Continuation-in-part of Ser. No. 787,069, Oct. 15, 1985, abandoned.

[51] Int. Cl.⁴ ................................................ A61L 9/00
[52] U.S. Cl. ......................................... 239/34; 239/57
[58] Field of Search ....................... 239/34, 37, 43, 44, 239/53–57, 6

[56] References Cited

U.S. PATENT DOCUMENTS

| | | | |
|---|---|---|---|
| 3,558,055 | 1/1971 | Storchheim | 239/55 X |
| 4,096,994 | 6/1978 | Bryson | 239/57 |
| 4,226,829 | 10/1980 | Mike | 239/55 X |
| 4,445,641 | 5/1984 | Baker et al. | 239/6 |

Primary Examiner—Andres Kashnikow
Attorney, Agent, or Firm—Edward J. Sites

[57] ABSTRACT

A device for dispensing volatile fragrances comprises a hollow body, and a liquid volatile fragrance contained within the hollow. The liquid volatile fragrance diffuses through a closure member made of a silicone rubber body, to the outer surface where it is volatilized to disperse in the surrounding atmosphere.

2 Claims, 2 Drawing Sheets

DEVICE FOR DISPENSING VOLATILE FRAGRANCES

CROSS-REFERENCE TO RELATED APPLICATION

This application is a continuation-in-part of my co-pending U.S. Patent Application Ser. No. 787,069 filed Oct. 15, 1985, now abandoned.

BACKGROUND OF THE INVENTION

1. Field of the Invention

The invention relates to an article of manufacture for the slow release of a volatile fragrance composition.

2. Brief Description of the Prior Art

Articles of many types for the controlled release of volatile compositions such as odorants or deodorants, to the environment, are well known in the art. However, articles which have heretofore been disclosed suffer from various disadvantages, especially with respect to performance. Ideally, an article for dispensing a volatile fragrance composition should dispense the composition unchanged at an essentially constant rate over an extended period of time, to provide an effective level of the fragrance in the environment, up to the time when the volatile composition contained within the article is depleted. This desirable property is termed a "linear release".

The so-called gel-type deodorizer dispensers in which a fragrance is dispersed in a water based gel are known and generally useful in that they provide acceptable levels of deodorant to the air environment. Release may be the desired linear release, but many dispensors of this type do not provide a linear release. Also, the gel-type dispensers suffer from the disadvantage that the lifetimes for fragrance release are relatively short, typically on the order of one or two weeks, due to rapid evaporation of water and fragrance from the gel formulation. An additional disadvantage of the gel-type dispensers is that only select fragrance compositions, which are compatible with the water-based gels, can be used in the gel formulations.

Articles comprised of a volatile dispersed in various polymeric resin substrates such as polyamides, ethylene-vinyl acetate copolymer, cross-linked methacrylate derivatives and the like have also been described in the prior art literature. These articles suffer from the disadvantage that levels of fragrance output are frequently too low to be effective for all purposes. These articles also generally provide a nonlinear release of fragrance, that is, the level of the fragrance output is typically high during the initial period of use but then drops off within a short period of time. An additional disadvantage of these articles is that many volatile fragrances are incompatible with the polymer substrates. This frequently results in sweating of the article surface, a situation where beads of fragrance material appears on the surface of the polymer substrate. A further disadvantage of the articles in which fragrances are dispersed in a solid polymer is that liquid fragrances must either be admixed with the polymer by melt blending at relatively high temperatures or mixed with the monomer prior to carrying out the polymerization reaction. In both instances, substantial degradation of fragrances may occur. Examples of polymeric articles of the aforementioned types are described in U.S. Pat. Nos. 4,095,031; 4,411,855; 3,926,655; 4,184,009 and Canadian Pat. No. 1,099,429. Also illustrative of such articles is that described in Japanese Patent Application No. 82-40,558. This latter reference describes a fragrant, rubber-like molding material, formed by dispersing a fragrance in a silicone rubber and then carrying out a cross-linking reaction with an organometal salt. The articles suffer from the disadvantage that severe sweatingof the silicone rubber occurs at even moderate loadings of volatile substances due to incompatibility of the silicone polymer and the fragrance.

Wick-type deodorizers have also been described in the prior art. Release of the deodorant may at times be linear. Although these reservoir-type systems are effective under limited conditions, the dispensers are generally objectionable in appearance. The wicks are sometimes prone to clogging and generally require deodorants which are suitable for water-based formulations.

The U.S. Pat. No. 4,161,283 describes a fragrance-dispensing pouch comprised of a fragrance-containing reservoir enclosed by an outer wall made of a fragrance (gas) permeable film, heat sealed to an impermeable inner wall. This device suffers from the disadvantage that it is not self-supporting and therefore cannot be conveniently located where desired. It is also difficult to manufacture and articles of this type cannot be made into a variety of desirable shapes. More importantly the fragrances which are desirably used in "air freshener" type devices are generally a complex blend of a large number of components having a wide variety of volatilities. As mentioned above, ideally there should be a uniform discharge of the total blend components over the entire life of the device, so as to emit the complete fragrance. The emission of the unchanged blend of ingredients, i.e., linear emission, has heretofore been difficult to obtain wth the pouch type of prior art devices. The fragrance when exposed to the air within the pouch will break down into its individual volatile components with the most volatile component passing through the reservoir wall without the remaining volatiles. Then in sequence, each of the next more volatile components vaporizes and passes through the reservoir wall. The serial release of the components of the fragrance composition may result in the observed fragrance having a substantially different odor over its intended life rather than a linear release, i.e., a constant and unchanging fragrance over a period of time. The problem of serial emission of the components of the fragrance rather than linear emission is encountered with all of the thin film gas permeable materials typically used in prior art devices, such as is described in U.S. Pat. No. 2,766,066 (Hopson et al.).

A dispenser is described in the U.S. Pat. No. 4,161,283 to Hyman which functions by molecular diffusion of a liquid volatile composition through a generally non-porous polymeric resin wall. This type of fragrance dispenser suffers from the disadvantage that all ingredients in a complex fragrance composition do not have the same molecular structure and will not diffuse through the polymeric resin walls at the same rates. The composition is changed as it is released, i.e., a non-linear release.

Also, it is generally well-known that the thicker the film of a polymer, the lower is the rate of gas or liqiuid permeability through the film. Accordingly, in order for polymer films such as polyethylene or polyvinyl chloride to have adequate permeability the film has to be either very thin or made mechanically porous with holes or like perforations; see U.S. Pat. No. 2,766,066, supra.

The articles of the present invention are particularly useful for the containment of a liquid form of a volatile fragrance composition and the sustained, slow release of a volatilized form of the composition to the atmosphere.

We have found that silicone rubbers have a unique property which makes relatively thick sections especially useful in air freshener devices. Silicone rubbers in addition to behaving like thin films of other polymers with regard to gas permeability, in relatively thick films, charge up or load up with the liquid fragrance composition, unchanged in regard to the relative amounts of each of the components in the fragrance composition. In other words, the liquid composition permeating the rubber will have the same ingredient make-up as the liquid composition held in the device's reservoir. Once the thick film of the silicone rubber material is charged up the unchanged liquid composition travels through and is evaporated in toto from the outer surface of the silicone rubber. It is important to note that the relative thickness of the silicone rubber, once it is thicker than the point where there is any substantial amount of gas permeability, does not affect the operation of the device except with regard to the time required to allow for fully charging of the entire thickness of the silicone rubber. The only factor which appears to have any effect on the dispensing of the fragrance material from an article of the invention is the amount of outer surface area which is exposed to the ambient air.

A difference between many of the prior art articles and the present invention is that the articles of the invention do not rely on gas permeation through a thin or porous membrane. Instead, liquid penetration as a uniform mixture through a relatively thick silicone rubber body provides linear release of fragrance composition ingredients.

Silicone rubbers have been described as functioning as reservoirs for the slow release of liquids to marine environments; See for example the U.S. Pat. No. 3,426,473 to Cardarelli et al. issued on Feb. 11, 1969. Also, impermeable housings supported on legs have been suggested to contain deodorants for dispensing; see U.S. Pat. No. 4,096,994 (Bryson).

SUMMARY OF THE INVENTION

The invention comprises an article for dispensing a volatile fragrance composition to the atmosphere, which comprises;
  A. an open-ended hollow body of a material which is substantially impermeable to said volatile composition;
  B. a liquid volatile fragrance composition contained in the hollow of said body;
  C. a silicone rubber closure having first and second surfaces, and a body between the surfaces, mounted in the open end of the hollow body and having the first surface in direct contact with the liquid volatile composition, and the second surface in contact with air outside of said body, said closure being permeable to said composition in a liquid form, said closure being substantially impermeable to the volatile composition in a volatilized form;
  D. a base attached to the open end of the hollow body, said base including means to allow circulation of air below the silicone rubber closure, in contact with the second surface of the closure;

said body being penetrable by said composition in a liquid form, at a rate less than the rate of volatilization of the liquid volatile composition as it reaches the second surface of the hollow body under ambient temperature and pressure conditions.

An advantage of the invention is that any volatile fragrance composition, including expensive perfume compositions, may be contained and slowly released from the article without any alteration of the composition or released aroma. The articles of the invention may be used for dispensing fragrances over a long period of time, as for example, several weeks or months. This device is advantageously used as an air freshener.

Another advantage of the invention is that the article reservoirs may be refilled with either the same or another volatile fragrance composition after the original charge has been depleted. This reusability is attractive to many consumers, due to real and perceived cost savings. It is also an attractive feature to the supplier of the fragrance composition because it encourages resale of their composition to the original purchaser of the dispenser article.

DETAILED DESCRIPTION OF THE PREFERRED EMBODIMENTS OF THE INVENTION

Figure 1:
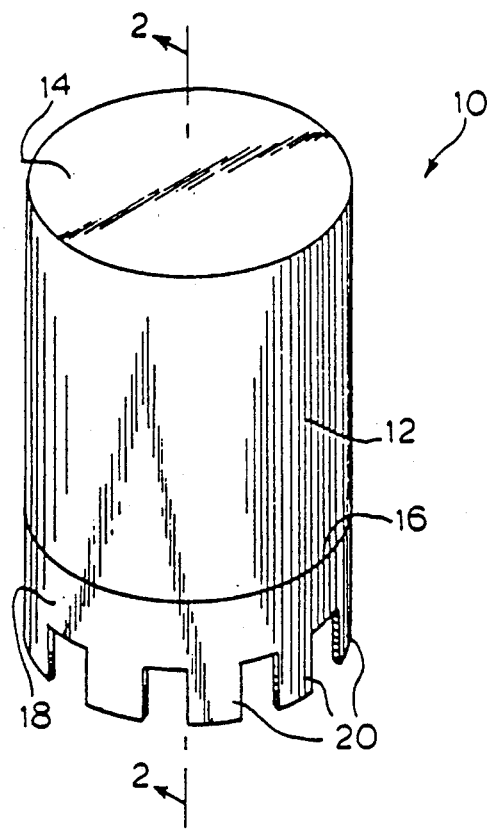
FIG. 1 is a perspective view of an open-ended hollow body to which is affixed by compression to the open end of the hollow body a disc made of silicone rubber.

Referring first to FIG. 1, a perspective view of an embodiment device 10 of the invention is seen. The device 10 comprises a cylindrical body 12 which may be fabricated from any conventional material such as metal, glass, synthetic polymeric resin and like materials which are impermeable to the volatile composition to be contained and dispensed. The body 12 has a closed end 14 and an open end 16 resting on a base cap 18 which is supported by legs 20 about the lower periphery of the base cap 18.

Figure 2:
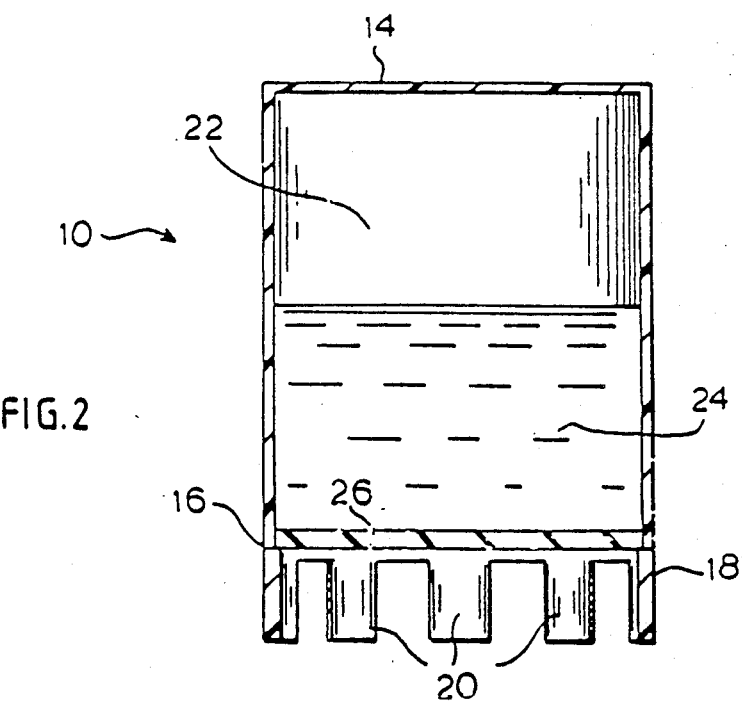
FIG. 2 is a cross-sectional view of the device depicted in FIG. 1, which shows the reservoir for containing the volatile substance, the silicone rubber disc, and a screw cap which functions to tightly hold the silicone rubber disc in plane and also functions as a base through which air is allowed to circulate by virtue of the base design.

Referring now to FIG. 2, a view along lines 2—2 of FIG. 1, further details of the device 10 may be seen including a chamber 22 defined by the walls of the body 12 and the ends 14, 16. The chamber 22 is filled or partially filled with a liquid volatile composition 24. A silicone rubber disc 26 is affixed to the open end 16 of the hollow body 12 and held tightly in place by the cap 18 which serves as a base for the device 10 and is also designed to allow circulation of air below the silicone rubber disc 26, between legs 20.

A silicone rubber is herein defined as a cross-linked silicone elastomer, preferably of the type vulcanized at room temperature (RTV) or at elevated temperatures (HTV). Such silicone rubbers are well known, as are methods of their preparation; see for example the descriptions given in the U.S. Pat. Nos. 3,664,997; 3,674,738; 4,180,642; 4,216,140; and 4,419,484, all of which are incorporated herein by reference thereto. Dimethyl siloxanediol with silicone resin or alkyl silicate as cross-linking agents are advantageously used. Generally, fillers such as silica, calcium carbonate, titanium oxide, and the like may be added to the polymer. The filler materials provide rigidity. Mica fillers can also be used to control porosity of the silicone rubber. Higher mica contents reduce vapor and gas transmission rates.

One example of a preferred silicone rubber used in the invention is the commercially available Dow Corning 3110 RTV silicone rubber. This material may be cross-linked at room temperature with Dow Corning RTV catalyst No. 4.

We have found that the silicone rubber disc 26 thickness is a limiting variable, in that relatively thick walls, as thick as about 1-2 mm to about 5 mm, will give uniform and high rates of release of volatile fragrance composition 24. Thinner walls tend to allow the passage of gases, including the volatilized form of the fragrance composition (when the device 10 is inverted during non-use as described below). As described above, this is undesirable, and may result in a nonlinear dispensing of the fragrance composition.

In actual use the liquid fragrance composition 24 is brought into contact with the thick body of silicone rubber 26 as shown in FIG. 2. The uniform mixture of the fragrance composition 24 charges up the silicone rubber disc 26 and travels to the outer surface where it can be exposed, unchanged, to the air. A uniform mixture of the fragrance composition constantly volatilizes from the outer surface and is replenished with fresh liquid fragrance composition 24 from within the body of the silicone rubber disc 26. It has been found that over the course of the entire use of a device 10 having the thick silicone rubber disc 26 that there is a uniform linear emission of the fragrance composition.

It will be appreciated that the liquid porosity of the silicone rubber disc 26 is a factor to be adjusted for in relation to the fluidity and penetration of the fragrance composition 24 and the rate at which it will transfer across the wall of disc 26. If the rate of travel is too fast, the liquid will accumulate on the outer surface of disc 26 faster than volatilization occurs. As mentioned above, this is a problem with many of the prior art devices. To avoid this, some trial and error testing may be necessary for specific combinations of silicone rubber (thickness and porosity) and fragrance compositions. In general however the silicone rubber may be selected from those having a water vapor transmission rate at 38° C., under a 90 percent room humidity of from 5 to 50 gms/24 hours/m² in a 70 mil. thick section (as determined by ASTM test method E-96-66, Condition E) and a gas (N) permeability coefficient of 50 to 100 gms/24 hours/m² at 23° C. and atmospheric pressure.

Figure 3:
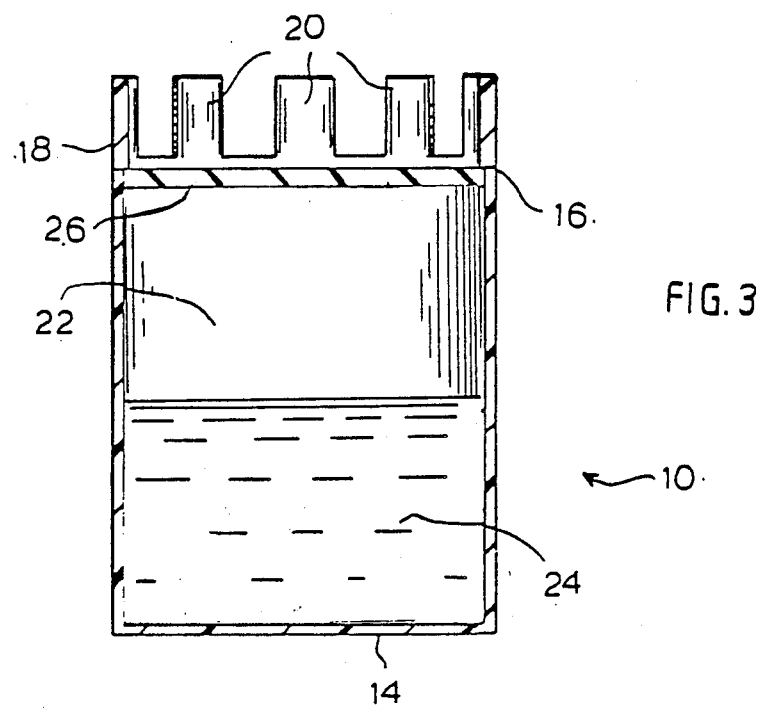
FIG. 3 is a view as in FIG. 2, but with the device inverted.

FIG. 3 is a cross-sectional side elevation of the embodiment device 10 of the invention shown in an inverted position. In this position the fragrance composition 24 is removed from contact with the disc 26. Since disc 26 is substantially impermeable to a volatilized form of composition 24, the device 10 is "switched off" and does not dispense the fragrance composition 24.

While there have been shown and described preferred embodiments of a device 10 for dispensing volatile compositions in accordance with the inventoion, it will be appreciated that many changes and modifications may be made without departing from the spirit of the invention. For example, the device 10 may be packaged for transportation and storage before use within an impermeable barrier layer or film such as a metal foil to further inhibit dispensing of the contained composition 24 prior to the time when release is desired.

The device 10 is particularly useful for the dispensing of complex fragrance composition 24. Fragrances which may be included in the complex compositions 24 are represented by natural essential oils such as lemon oil, mandarin oil, clove leaf oil, petitgrain oil, cedar wood oil patchoulli oil, lavandin oil, neroli oil, ylang oil, rose absolute or jasmin absolute; natural resins such as labdanum resin or olibanum resin; single perfumery chemicals which may be isolated from natural sources or manufactured synthetically, as for example alcohols such as geraniol, nerol, citronellol, linalool, tetrahydrogeraniol, betaphenylethyl alcohol, methyl phenyl carbinol, dimethyl benzyl carbinol, menthol or cedrol; acetates and other esters derived from such alcohols-aldehydes such as citral, citronellal, hydroxycitronellal, lauric aldehyde, undecylenic aldehyde, cinnamaldehyde, amyl cinnamic aldehyde, vanillin or heliotropin; acetals derived from such aldehydes; ketones such as methyl hexyl ketone, the ionones and the methylionones; phenolic compounds such as eugenol and isoeugenol; synthetic musks such as musk xylene, musk ketone and ethylene brassylate and the like.

Generally, the fragrances as represented above are compounded in mixtures with perfumery acceptable carriers to obtain the compositions 24.

Perfumery acceptable carriers are well known and are represented by a volatile liquid, such as a non-toxic alcohol (e.g. ethyl alcohol), a non-toxic glycol (e.g. 1,2-propylene glycol) and the like.

The compositions 24 as part of the articles of the invention may be prepared by a simple, homogeneous admixture of the carrier and the fragrance ingredient or ingredients.

The following example describes the manner and process of making and using the invention and sets forth the best mode contemplated by the inventor for carrying out the invention but are non-limiting of the invention. All parts are by weight unless otherwise stated. Where reported, the following test methods are employed: Tensile strength, ASTM test method D-638; elongation, ASTM test method D-638; Shore A hardness, ASTM test method D-2240; moisture vapor transmission rate; ASTM test method E-96-66 (condition E).

EXAMPLE

There is mixed with 480 parts of silanol end-stopped dimethylpolysiloxane of 4200 centipoise viscosity at 25° C., 120 parts of trimethylsiloxy end-stopped, silanol end-stopped polysiloxane oil, and 18 parts of a cyclicsiloxane treated fumed silica and 480 parts of 160 mesh mica which is treated with 4% by weight of stearic acid. To 100 parts of the above composition there is added 10 parts of a catalyst composition prepared by mixing 102 parts of a vinyl terminated dimethylpolysiloxane of 3,000 cps at 25° C., 120 parts of $CaCo_3$, 48 parts of gamma aminopropyltriethoxysilane, 24 parts of partially hydrolyzed ethyl silicate and 3.6 parts of dibutyl tin dilaurate.

Sample sheets of the compositions which have cured for 24 hours at 25° C. give the following physicals and moisture vapor transmission rate (MVTR):

Tensile Strength psi: 330
Elongation %: 70
Shore A Hardness: 62

MVTR-8.25 grams/M² on sheet 74 mils thick.

A container article as shown in the accompanying drawing of FIG. 1 is molded from a polystyrene and closed with a silicone rubber disc molded from the above described silicone rubber, having a minimum wall thickness of about 5 mm and a container capacity of about 25 gms of a liquid fragrance composition prepared by simple admixture of the following ingredients.

|  | Parts |
| --- | --- |
| phenyl ethyl alcohol extra | 27.00 |
| linalol pure | 10.00 |
| benzyl acetate | 14.00 |
| lilestralis | 7.00 |
| amyl cinnamic aldehyde | 7.00 |
| alpha terpineol | 10.00 |
| gamma methyl ionone | 5.00 |
| aldehyde C11 - lenic | 0.50 |
| coumarin crystals | 3.00 |
| terpinyl acetate | 1.50 |
| para-tert-butyl-cycloxyl acetate | 10.00 |
| diethyl phthalate | 5.00 |
|  | 100.00 |

The fragrance composition, which has a woody, ambre character, is charged to the device 10 and the device is placed in an open room for a period of about 6 weeks. At that time, a second device is charged with a freshly prepared fragrance composition as described above. A panel of odor analysts is assembled and asked to evaluate the odor emanating from the two containers and from the freshly prepared composition. A majority of the panel will agree that they cannot distinguish the three sources of fragrance.

In perfume compositions, it is the individual components which contribute their particular olfactory characteristics. However, the overall sensory effect of the perfume composition will be at least the sum total of the effects of each of the ingredients. It can be concluded that the volatilized and dispensed fragrances described in this example are unchanged in their passage to the atmosphere. There is a linear release.

What is claimed is:

1. An article for dispensing a volatile fragrance composition to the atmosphere, which comprises;
   A. an open-ended hollow body of a material which is substantially impermeable to said volatile composition;
   B. a liquid volatile fragrance composition contained in the hollow of said body;
   C. a silicone rubber closure having first and second surfaces, and a body between the surfaces, mounted in the open end of the hollow body and having the first surface in direct and full contact with the liquid volatile composition, and the second surface in contact with the atmosphere outside of said body, said closure being permeable to said composition in a liquid form, said closure being substantially impermeable to the volatile composition in a volatilized form;
   D. A base attached to the open end of the hollow body, said base including means to allow circulation of air below the silicone rubber closure, in contact with the second surface of the closure; said body being penetrable by said composition in a liquid form, at a rate less than the rate of volatilization of the liquid volatile composition as it reaches the second surface of the hollow body under ambient temperature and pressure conditions.

2. The device of claim 1 wherein the silicone rubber closure has a thickness of from about 1 to about 5 mm.

* * * * *